US007012127B1

(12) United States Patent
Araña Rosainz et al.

(10) Patent No.: US 7,012,127 B1
(45) Date of Patent: Mar. 14, 2006

(54) ANALOGUES OF LIPOPOLYSACCHARIDE-BINDING PROTEIN (LBP)-DERIVED PEPTIDES THAT EFFICIENTLY NEUTRALIZE LIPOPOLYSACCHARIDES (LPS)

(75) Inventors: Manuel de Jesús Araña Rosainz, Ciudad de la Habana (CU); Glay Chinea Santiago, Ciudad de la Habana (CU); Maribel Guerra Vallespi, Ciudad de la Habana (CU); Osvaldo Reyes Acosta, Ciudad de la Habana (CU)

(73) Assignee: Centro de Ingenicria Genetica y Biotecnologia, Cuidad de la Habana (CU)

( * ) Notice: Subject to any disclaimer, the term of this patent is extended or adjusted under 35 U.S.C. 154(b) by 323 days.

(21) Appl. No.: 09/588,525

(22) Filed: Jun. 6, 2000

(30) Foreign Application Priority Data

Jun. 10, 1999 (CU) .................................... 1999/71

(51) Int. Cl.
*C07K 14/00* (2006.01)
*C07K 16/00* (2006.01)
*C07K 17/00* (2006.01)

(52) U.S. Cl. ...................... 530/300; 530/323; 530/326; 530/327

(58) Field of Classification Search .................. 514/12, 514/8, 14; 530/350, 300, 323, 326, 327; 435/240

See application file for complete search history.

(56) References Cited

U.S. PATENT DOCUMENTS 5,731,415 A * 3/1998 Gazzano-Santoro et al. ..... 530/350

FOREIGN PATENT DOCUMENTS

| | | |
|---|---|---|
| WO | WO 95/00641 | 1/1995 |
| WO | WO 95/05393 | 2/1995 |
| WO | WO 95/08560 | 3/1995 |
| WO | WO 95/25117 | 9/1995 |

OTHER PUBLICATIONS

Accession No. AAW40153 sequence alingment.*

Norbert Lamping, et al., "Effects of Site-Directed Mutagenesis of Basic Residues (Arg 94, Lys 95, Lys 99) of Lipopolysaccharide (LPS)-Binding Protein on Binding and Transfer of LPS and Subsequent Immune Cell Activation", *The Journal of Immunology*, vol. 157, pp. 4648-4656 (1996).

Manuel J. Araña, et al., "Molecules Modulating Immune/Inflammatory Responses, Design and Development of Potential Therapeutics", *Biotecnologia Applicada*, vol. 12, No. 2, pp. 101-102 (1995).

* cited by examiner

*Primary Examiner*—Mark Navarro
(74) *Attorney, Agent, or Firm*—Hoffmann & Baron, LLP

(57) ABSTRACT

The present invention relates to analogues of peptides from lipopolysaccharide-binding protein (LBP) region whose primary sequence have been substituted at particular amino acid sites to obtain effective binding to, and neutralization of, lipopolysaccharide (LPS).

15 Claims, 3 Drawing Sheets

SEQUENCE LISTING

```
<160> NUMBER OF SEQ ID NOS: 56

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
```

-continued

```
<223> OTHER INFORMATION: /note="LBP 86-99"
<223> OTHER INFORMATION: Description of Artificial Sequence: peptide
      with an amino acid sequence derived from LBP mature protein

<400> SEQUENCE: 1

Arg Val Gln Gly Arg Trp Lys Val Arg Lys Ser Phe Phe Lys
  1               5                  10


<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="(LBP A86) Example of a peptide of the
      invention comprising one or more selected
      substitutions at particular site(s) compared to the
      peptide of SEQ ID NO 1"

<400> SEQUENCE: 2

Ala Val Gln Gly Arg Trp Lys Val Arg Lys Ser Phe Phe Lys
  1               5                  10


<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="(LBP A90) Example of a peptide of the
      invention comprising one or more selected
      substitutions at particular site(s) compared to the
      peptide of SEQ ID NO 1"

<400> SEQUENCE: 3

Arg Val Gln Gly Ala Trp Lys Val Arg Lys Ser Phe Phe Lys
  1               5                  10


<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="(LBP A94) Example of a peptide of the
      invention comprising one or more selected
      substitutions at particular site(s) compared to the
      peptide of SEQ ID NO 1"

<400> SEQUENCE: 4

Arg Val Gln Gly Arg Trp Lys Val Ala Lys Ser Phe Phe Lys
  1               5                  10


<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="(LBP A95) Example of a peptide of the
      invention comprising one or more selected
      substitutions at particular site(s) compared to the
      peptide of SEQ ID NO 1"
```

-continued

```
<400> SEQUENCE: 5

Arg Val Gln Gly Arg Trp Lys Val Arg Ala Ser Phe Phe Lys
  1               5                  10


<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="(LBP A96) Example of a peptide of the
      invention comprising one or more selected
      substitutions at particular site(s) compared to the
      peptide of SEQ ID NO 1"

<400> SEQUENCE: 6

Arg Val Gln Gly Arg Trp Lys Val Arg Lys Ala Phe Phe Lys
  1               5                  10


<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="(LBP A98) Example of a peptide of the
      invention comprising one or more selected
      substitutions at particular site(s) compared to the
      peptide of SEQ ID NO 1"

<400> SEQUENCE: 7

Arg Val Gln Gly Arg Trp Lys Val Arg Lys Ser Phe Ala Lys
  1               5                  10


<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention
      comprising one or more selected substitutions at
      particular site(s) compared to the peptide of
      SEQ ID NO 1"

<400> SEQUENCE: 8

Ala Val Gln Gly Arg Trp Lys Val Arg Lys Ser Phe Ala Lys
  1               5                  10


<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention
      comprising one or more selected substitutions at
      particular site(s) compared to the peptide of
      SEQ ID NO 1"

<400> SEQUENCE: 9
```

-continued

```
Ala Val Gln Gly Arg Trp Lys Val Arg Ala Ser Phe Phe Lys
  1               5                   10


<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention
      comprising one or more selected substitutions at
      particular site(s) compared to the peptide of
      SEQ ID NO 1"

<400> SEQUENCE: 10

Ala Val Gln Gly Ala Trp Lys Val Arg Lys Ser Phe Phe Lys
  1               5                   10


<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention
      comprising one or more selected substitutions at
      particular site(s) compared to the peptide of
      SEQ ID NO 1"

<400> SEQUENCE: 11

Ala Val Gln Gly Arg Trp Lys Val Ala Lys Ser Phe Phe Lys
  1               5                   10


<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention
      comprising one or more selected substitutions at
      particular site(s) compared to the peptide of
      SEQ ID NO 1"

<400> SEQUENCE: 12

Ala Val Gln Gly Arg Trp Lys Val Arg Lys Ala Phe Phe Lys
  1               5                   10


<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention
      comprising one or more selected substitutions at
      particular site(s) compared to the peptide of
      SEQ ID NO 1"

<400> SEQUENCE: 13

Arg Val Gln Gly Ala Trp Lys Val Ala Lys Ser Phe Phe Lys
  1               5                   10
```

-continued

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention comprising one or more selected substitutions at particular site(s) compared to the peptide of SEQ ID NO 1"

<400> SEQUENCE: 14

Arg Val Gln Gly Ala Trp Lys Val Arg Ala Ser Phe Phe Lys
1 5 10

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention comprising one or more selected substitutions at particular site(s) compared to the peptide of SEQ ID NO 1"

<400> SEQUENCE: 15

Arg Val Gln Gly Ala Trp Lys Val Arg Lys Ala Phe Phe Lys
1 5 10

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention comprising one or more selected substitutions at particular site(s) compared to the peptide of SEQ ID NO 1"

<400> SEQUENCE: 16

Arg Val Gln Gly Arg Trp Lys Val Ala Lys Ala Phe Phe Lys
1 5 10

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention comprising one or more selected substitutions at particular site(s) compared to the peptide of SEQ ID NO 1"

<400> SEQUENCE: 17

Arg Val Gln Gly Arg Trp Lys Val Ala Lys Ser Phe Ala Lys
1 5 10

<210> SEQ ID NO 18
<211> LENGTH: 14

-continued

```
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention
      comprising one or more selected substitutions at
      particular site(s) compared to the peptide of
      SEQ ID NO 1"

<400> SEQUENCE: 18

Arg Val Gln Gly Arg Trp Lys Val Arg Lys Ala Phe Ala Lys
  1               5                  10


<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention
      comprising one or more selected substitutions at
      particular site(s) compared to the peptide of
      SEQ ID NO 1"

<400> SEQUENCE: 19

Arg Val Gln Gly Arg Trp Lys Val Arg Ala Ser Phe Ala Lys
  1               5                  10


<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention
      comprising one or more selected substitutions at
      particular site(s) compared to the peptide of
      SEQ ID NO 1"

<400> SEQUENCE: 20

Arg Phe Gln Gly Arg Trp Lys Val Arg Ala Ser Phe Phe Lys
  1               5                  10


<210> SEQ ID NO 21
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention
      comprising one or more selected substitutions at
      particular site(s) compared to the peptide of
      SEQ ID NO 1"

<400> SEQUENCE: 21

Arg Val Asn Gly Arg Trp Lys Val Arg Ala Ser Phe Phe Lys
  1               5                  10


<210> SEQ ID NO 22
<211> LENGTH: 14
<212> TYPE: PRT
<213> ORGANISM: Artificial Sequence
<220> FEATURE:
```

-continued

```
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention
      comprising one or more selected substitutions at
      particular site(s) compared to the peptide of
      SEQ ID NO 1"

<400> SEQUENCE: 22

Arg Val Gln Met Arg Trp Lys Val Arg Ala Ser Phe Phe Lys
  1               5                  10


<210> SEQ ID NO 23
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention
      comprising one or more selected substitutions at
      particular site(s) compared to the peptide of
      SEQ ID NO 1"

<400> SEQUENCE: 23

Arg Val Gln Phe Arg Trp Lys Val Arg Ala Ser Phe Phe Lys
  1               5                  10


<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention
      comprising one or more selected substitutions at
      particular site(s) compared to the peptide of
      SEQ ID NO 1"

<400> SEQUENCE: 24

Arg Val Gln Gly Arg Trp Lys Phe Arg Ala Ser Phe Phe Lys
  1               5                  10


<210> SEQ ID NO 25
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention
      comprising one or more selected substitutions at
      particular site(s) compared to the peptide of
      SEQ ID NO 1"

<400> SEQUENCE: 25

Arg Val Gln Gly Arg Trp Lys Val Arg Ala Gln Phe Phe Lys
  1               5                  10


<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
```

-continued

<223> OTHER INFORMATION: /note="Example of a peptide of the invention comprising one or more selected substitutions at particular site(s) compared to the peptide of SEQ ID NO 1"

<400> SEQUENCE: 26

Arg Val Gln Gly Arg Trp Lys Val Arg Ala Ser Trp Phe Lys
1 5 10

<210> SEQ ID NO 27
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention comprising one or more selected substitutions at particular site(s) compared to the peptide of SEQ ID NO 1"

<400> SEQUENCE: 27

Arg Val Gln Gly Arg Trp Lys Val Arg Ala Ser Phe Phe Ala
1 5 10

<210> SEQ ID NO 28
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention comprising one or more selected substitutions at particular site(s) compared to the peptide of SEQ ID NO 1"

<400> SEQUENCE: 28

Arg Val Gln Gly Arg Trp Lys Val Arg Ala Ser Phe Gln Val
1 5 10

<210> SEQ ID NO 29
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention comprising one or more selected substitutions at particular site(s) compared to the peptide of SEQ ID NO 1"

<400> SEQUENCE: 29

Ala Val Gln Gly Arg Trp Lys Val Arg Ala Ser Phe Thr Val
1 5 10

<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention comprising one or more selected substitutions at particular site(s) compared to the peptide of -continued

```
      SEQ ID NO 1"

<400> SEQUENCE: 30

Arg Val Gln Gly Arg Trp Lys Val Arg Val Ser Phe Phe Lys
  1               5                  10


<210> SEQ ID NO 31
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention
      comprising one or more selected substitutions at
      particular site(s) compared to the peptide of
      SEQ ID NO 1"

<400> SEQUENCE: 31

Ala Val Gln Gly Arg Trp Lys Val Arg Val Ser Phe Phe Lys
  1               5                  10


<210> SEQ ID NO 32
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention
      comprising one or more selected substitutions at
      particular site(s) compared to the peptide of
      SEQ ID NO 1"

<400> SEQUENCE: 32

Arg Val Gln Gly Arg Trp Lys Val Arg Val Ser Phe Ala Lys
  1               5                  10


<210> SEQ ID NO 33
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention
      comprising one or more selected substitutions at
      particular site(s) compared to the peptide of
      SEQ ID NO 1"

<400> SEQUENCE: 33

Arg Val Gln Gly Arg Trp Lys Val Arg Val Ser Phe Gln Val
  1               5                  10


<210> SEQ ID NO 34
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention
      comprising one or more selected substitutions at
      particular site(s) compared to the peptide of
      SEQ ID NO 1"

<400> SEQUENCE: 34
```

-continued

```
Arg Val Gln Gly Arg Trp Lys Val Arg Val Thr Phe Phe Lys
  1               5                  10


<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention
      comprising one or more selected substitutions at
      particular site(s) compared to the peptide of
      SEQ ID NO 1"

<400> SEQUENCE: 35

Arg Val Gln Gly Arg Trp Arg Val Arg Val Lys Phe Thr Val
  1               5                  10


<210> SEQ ID NO 36
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention
      comprising one or more selected substitutions at
      particular site(s) compared to the peptide of
      SEQ ID NO 1"

<400> SEQUENCE: 36

Arg Val Gln Gly Arg Trp Arg Val Arg Val Ala Phe Ala Lys
  1               5                  10


<210> SEQ ID NO 37
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention
      comprising one or more selected substitutions at
      particular site(s) compared to the peptide of
      SEQ ID NO 1"

<400> SEQUENCE: 37

Ala Val Gln Gly Arg Trp Arg Val Arg Val Ser Phe Ala Lys
  1               5                  10


<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention
      comprising one or more selected substitutions at
      particular site(s) compared to the peptide of
      SEQ ID NO 1"

<400> SEQUENCE: 38

Ala Val Gln Gly Arg Trp Arg Val Arg Val Ser Phe Gln Val
  1               5                  10
```

-continued

```
<210> SEQ ID NO 39
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention
      comprising one or more selected substitutions at
      particular site(s) compared to the peptide of
      SEQ ID NO 1"

<400> SEQUENCE: 39

Arg Val Ser Gly Arg Trp Arg Val Arg Val Ser Phe Gln Val
  1               5                  10


<210> SEQ ID NO 40
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention
      comprising one or more selected substitutions at
      particular site(s) compared to the peptide of
      SEQ ID NO 1"

<400> SEQUENCE: 40

Arg Val Gln Gly Arg Trp Arg Val Arg Val Thr Phe Gln Val
  1               5                  10


<210> SEQ ID NO 41
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention
      comprising one or more selected substitutions at
      particular site(s) compared to the peptide of
      SEQ ID NO 1"

<400> SEQUENCE: 41

Arg Val Gln Gly Arg Trp Arg Val Ala Lys Ser Phe Gln Val
  1               5                  10


<210> SEQ ID NO 42
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention
      comprising one or more selected substitutions at
      particular site(s) compared to the peptide of
      SEQ ID NO 1"

<400> SEQUENCE: 42

Ala Val Gln Gly Arg Trp Arg Val Ala Lys Ser Phe Gly Lys
  1               5                  10


<210> SEQ ID NO 43
```

-continued

```
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention
      comprising one or more selected substitutions at
      particular site(s) compared to the peptide of
      SEQ ID NO 1"

<400> SEQUENCE: 43

Ala Val Gln Gly Arg Trp Arg Val Ala Lys Ser Phe Gln Val
  1             5                   10


<210> SEQ ID NO 44
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention
      comprising one or more selected substitutions at
      particular site(s) compared to the peptide of
      SEQ ID NO 1"

<400> SEQUENCE: 44

Ala Val Ser Gly Arg Trp Arg Val Ala Lys Ala Phe Gly Lys
  1             5                   10


<210> SEQ ID NO 45
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention
      comprising one or more selected substitutions at
      particular site(s) compared to the peptide of
      SEQ ID NO 1"

<400> SEQUENCE: 45

Arg Val Gln Gly Ala Trp Lys Val Arg Ala Ser Phe Ala Lys
  1             5                   10


<210> SEQ ID NO 46
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention
      comprising one or more selected substitutions at
      particular site(s) compared to the peptide of
      SEQ ID NO 1"

<400> SEQUENCE: 46

Arg Val Gln Gly Ala Trp Lys Val Arg Ala Ser Phe Gln Val
  1             5                   10


<210> SEQ ID NO 47
<211> LENGTH: 14
<212> TYPE: PRT
<213> ORGANISM: Artificial Sequence
```

-continued

```
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention
      comprising one or more selected substitutions at
      particular site(s) compared to the peptide of
      SEQ ID NO 1"

<400> SEQUENCE: 47

Ala Val Gln Gly Ala Trp Lys Val Arg Ala Ser Phe Ala Lys
  1               5                  10


<210> SEQ ID NO 48
<211> LENGTH: 14
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(14)
<223> OTHER INFORMATION: /note="Example of a peptide of the invention
      comprising one or more selected substitutions at
      particular site(s) compared to the peptide of
      SEQ ID NO 1"

<400> SEQUENCE: 48

Ala Val Gln Gly Ala Trp Lys Val Arg Ala Ser Phe Gln Val
  1               5                  10


<210> SEQ ID NO 49
<211> LENGTH: 18
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(18)
<223> OTHER INFORMATION: /note="Example of a peptide of the invention
      comprising one or more selected substitutions at
      particular site(s) compared to the peptide of
      SEQ ID NO 1"

<400> SEQUENCE: 49

Thr Ile Arg Val Gln Gly Arg Trp Lys Val Arg Ala Ser Phe Phe Lys
  1               5                  10                  15

Leu Gln


<210> SEQ ID NO 50
<211> LENGTH: 18
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(18)
<223> OTHER INFORMATION: /note="Example of a peptide of the invention
      comprising one or more selected substitutions at
      particular site(s) compared to the peptide of
      SEQ ID NO 1"

<400> SEQUENCE: 50

Thr Val Arg Val Gln Gly Ala Trp Lys Val Arg Ala Ser Phe Phe Lys
  1               5                  10                  15

Leu Gln


<210> SEQ ID NO 51
<211> LENGTH: 18
<212> TYPE: PRT
```

-continued

```
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(18)
<223> OTHER INFORMATION: /note="Example of a peptide of the invention
      comprising one or more selected substitutions at
      particular site(s) compared to the peptide of
      SEQ ID NO 1"

<400> SEQUENCE: 51

Thr Val Arg Val Gln Gly Arg Trp Lys Val Arg Ala Ser Phe Ala Lys
  1               5                  10                  15

Leu Gln


<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: peptide
<221> NAME/KEY: PEPTIDE
<222> LOCATION: (1)..(17)
<223> OTHER INFORMATION: /note="Example of a peptide of the invention
      comprising one or more selected substitutions at
      particular site(s) compared to the peptide of
      SEQ ID NO 1"

<400> SEQUENCE: 52

Ser Val Arg Val Gln Gly Arg Trp Lys Val Arg Ala Ser Phe Ala Val
  1               5                  10                  15

Thr


<210> SEQ ID NO 53
<211> LENGTH: 14
<212> TYPE: PRT
<213> ORGANISM: Artificial Sequence
<220> FEATURE:
<223> OTHER INFORMATION: Description of Artificial Sequence: example of
      a peptide substituted, in regard to the LBP primary sequence
<221> NAME/KEY: PEPTIDE
<222> LOCATION: (1)..(14)
<223> OTHER INFORMATION: /note="LBP A92"

<400> SEQUENCE: 53

Arg Val Gln Gly Arg Trp Ala Val Arg Lys Ser Phe Phe Lys
  1               5                  10


<210> SEQ ID NO 54
<211> LENGTH: 14
<212> TYPE: PRT
<213> ORGANISM: Artificial Sequence
<220> FEATURE:
<223> OTHER INFORMATION: Description of Artificial Sequence: example of
      a peptide substituted, in regard to the LBP primary sequence
<221> NAME/KEY: PEPTIDE
<222> LOCATION: (1)..(14)
<223> OTHER INFORMATION: /note="LBP A97"

<400> SEQUENCE: 54

Arg Val Gln Gly Arg Trp Lys Val Arg Lys Ser Ala Phe Lys
  1               5                  10


<210> SEQ ID NO 55
<211> LENGTH: 14
<212> TYPE: PRT
<213> ORGANISM: Artificial Sequence
<220> FEATURE:
<223> OTHER INFORMATION: Description of Artificial Sequence: example of
```

-continued

```
      a peptide substituted, in regard to the LBP primary sequence
<221> NAME/KEY: PEPTIDE
<222> LOCATION: (1)..(14)
<223> OTHER INFORMATION: /note="LBP A91"

<400> SEQUENCE: 55

Arg Val Gln Gly Arg Ala Lys Val Arg Lys Ser Phe Phe Lys
  1               5                  10


<210> SEQ ID NO 56
<211> LENGTH: 14
<212> TYPE: PRT
<213> ORGANISM: Artificial Sequence
<220> FEATURE:
<223> OTHER INFORMATION: Description of Artificial Sequence: peptide
      LBP-H

<400> SEQUENCE: 56

Gln Gly Arg Trp Lys Val Arg Lys Ser Phe Phe Lys Leu Gln
  1               5                  10
```

ANALOGUES OF LIPOPOLYSACCHARIDE-BINDING PROTEIN (LBP)-DERIVED PEPTIDES THAT EFFICIENTLY NEUTRALIZE LIPOPOLYSACCHARIDES (LPS)

This application claims priority to Cuban application No. CU1999/71, filed on Jun. 10, 1999.

The present invention relates generally to analogues of peptides from a LBP region whose primary sequence have been substituted at particular amino acid (a.a.) sites to obtain an effective binding to and neutralization of LPS; and specifically to the use of the peptides, and their derivatives, to prevent and treat sepsis and other endotoxin-related disorders.

Systemic inflammatory responses can be triggered by both infectious and not infectious disorders, such as severe trauma and pancreatitis. Sepsis include those manifestations related to the systemic response to infection, like tachycardia, tachypnea, chills, initial irregularly remittent fever followed by persistent fever, and leukocytosis, and those related to the organs dysfunction, such as cardiovascular, respiratory, renal, hepatic and hematological abnormalities. Sepsis is considered severe when it is associated with signs of hypoperfusion, like lactic acidosis, oliguria and altered mental status, with hypotension leading to shock, or with disseminated intravascular coagulation, adult respiratory distress syndrome and multiple organ failure.

Toxins produced or released by diverse microorganisms initiates the sepsis pathogenic cascade. Although septic shock is often only associated with Gram-negative bacteremia, Gram-positive bacteria, fungi, viruses, protozoa, spirochetes, rickettsiae, and inclusive plans and venoms can produce septic shock syndromes. *E. coli* is the most commonly isolated Gram-negative pathogen in sepsis, followed by *Klebsiella-Enterobacter*, and other bacteria such as *Pseudomonas, Proteus* and *Serratia*. Also *Neisseria meningitidis* bacteremia is a frequent cause of septic shock.

The process begins with the colonization by microorganisms of a tissue nidus. Then the organisms may invade bloodstream directly (bacteremia) or may proliferate locally and release toxic substances into the bloodstream (toxemia). Among these released substances, endotoxin, an structural component of gram-negative bacteria outer membrane is commonly associated with sepsis.

Endotoxin or lipopolysaccharide (LPS) is an ubiquitous component in the external leaf of the outer membrane of all Gram-negative bacteria. LPS biological and pharmacological activities are quite similar regardless the particular microorganisms they were derived of, or the specific strain pathogenicity. Structural differences are observed in endotoxin derived from different gram-negative bacterial strains. The outermost part of the endotoxin molecule consists of a series of oligosaccharides that are structurally and antigenically diverse. Internal to this oligosaccharides are the core saccharides which are structurally rather similar in gram-negative bacteria. To the core oligosaccharide is bound a lipid moiety, lipid A, highly conserved structure that is responsible for most LPS toxicity and biological activities.

LPS triggers both humoral and cell activation mechanisms that have a primary pathogenic role in shock and organ failure. Various humoral pathways are activated by LPS including the complement, coagulation and kallikrein cascades, which are partially responsible for haemodinamic changes observed in sepsis. Nevertheless, interactions between LPS and cellular receptors in a variety of cell types play a pivotal role in the biological and toxic effects of LPS. Particularly cells of the monocyte/macrophage lineage are involved in the host primary response to endotoxin. Other implicated cell types are polymorphonuclear (PMN) leukocytes and endothelial cells. Activation of these cell types by LPS is characterized by the rapid production and released of a series of products that constitute central endogenous mediators of sepsis, especially different cytokines such as TNF, IL-1 and IL-6.

The intravascular activation of inflammatory systems involved in septic shock, as the haemodinamic alterations, are mainly the consequence of a dysregulation in the production of these cytokines. One of them, TNF, is now regarded as a central mediator of the pathophysiological changes associated with LPS release. Therefore experimental approaches that inhibits TNF release induced by LPS are attractive as potential procedures to reduce sepsis morbidity and mortality.

LPS interacts with cellular receptors that are linked to signal pathways mediating cellular activation. CD14 is a membrane glycerolphosphorylinositol-anchored protein (mCD14) that is currently considered the major cellular receptor for LPS in myeloid cells[1]. Another protein, LBP, promotes interaction between LPS and mCD14 to form a high affinity complex. LBP enhances the binding of LPS to the membrane form of CD14, forming a ternary complex LBP:LPS:CD14. A soluble form of CD14 (sCD14) is also present in serum and it forms complexes with LPS that activates LPS-responsive cells lacking mCD14 such as endothelial, smooth muscle and epithelial cells[2]. LBP plays a catalytic role in the formation of LPS:sCD14 complexes for binding to non-mCD14 bearing cells. Therefore LBP plays a critical function in LPS-mediated cell activation events observed in sepsis; molecules that have the ability to compete or inhibit LBP enhancing effects in LPS biologic functions, could contribute definitively to ameliorate symptoms of sepsis.

During the last decade various agents that neutralize LPS effects have been described, and some of them are currently under preclinical or clinical development. Mortality induced by endotoxin administration was reduced in experimental animals pre-treated with anti-LPS antibodies[3]. Inasmuch as the N-terminal fragment of bactericidal/permeability increasing protein (BPI) keeps holoprotein's antiendotoxic and bactericial properties[4], this fragment have been used in preclinical, and recently in clinical trials to asses its effectiveness in the treatment of LPS-associated disorders such as meningococcemia, hemorrhagic trauma and severe intra-abdominal infections.

BPI-derived peptides and their analogues have been evaluated as endotoxin antagonists[5–8]. Among other peptide agents that bind to and neutralize LPS are those derived from *Limulus* anti-LPS factor (LALF)[9] and the synthetic antiendotoxin peptides mimicking polymyxin B structure.

The N-terminal fragment of LBP[10], as well as other shorter peptides, including 17–45, 65–108 and 142–169 regions, or segments thereof[6,11–14], have been described as LPS binding regions and their neutralizing ability over LPS toxic effects have been demonstrated.

DETAILED DESCRIPTION OF THE INVENTION

The present invention relates to analogues of peptide sequences derived from a LBP region, which result from substitutions within the primary structure of the native protein, and have an improved ability to bind and neutralize LPS biological effects. The above mentioned a.a. substitutions render peptides with advantageous properties when compare with previously described overlapping sequences[6, 10–14].

To understand the molecular basis of LPS-protein interaction the a.a. sequence of LBP and BPI, proteins known to bind specifically LPS, were analyzed. The aim of the study was to detect features in the primary structure of these proteins that could be correlated with the ability to interact with LPS. The analysis included predictions of secondary structure and accessibility, sequence similarity searches, inspection of conserved residues and analysis of the distribution of charged residues along the sequence. Inspection of the alignment reveals that some linear clusters of basic residues are present in LBP and BPI. These moieties could favorably interact with acidic groups of the highly anionic LPS (Lipid A). The basic character of these regions was specific of BPI and LBP; corresponding a.a. in other proteins from the same family are mainly neutral, with some aromatic residues. This fact could reflect differences between ligands: phospholipid transfer protein (PLTP) and cholesteryl ester transfer protein (CETP) bind specifically phospholipids and lipoproteins, respectively.

The analysis suggested that a potential LPS-binding site in LBP is located between residues 89 and 96 of the mature protein, considering a major cluster of basic residues in this region[14]. Other authors also proposed this, or overlapping sequences, as potential LPS-binding sites in LBP[6,11–13,15].

To corroborate this hypothesis, synthetic peptides corresponding to this region, including or not selected substitutions in specific residues were designed, synthesized and tested[14].

This invention provides peptides whose sequences result from single or multiple a.a substitutions at selected sites of the series, regarding the native sequence, which optimize the neutralizing capacity of the analogues.

In a first embodiment the invention relates to peptides characterized by their ability to antagonize the LBP:LPS interaction and to inhibit the biological effects triggered by LPS. The peptides of this invention present essential a.a. at positions +1, +5, +6, +7, +9, +10, +11, +12 and +13, and other preferred a.a. in other positions within the described sequences, all necessary for the optimal display of the LPS-neutralizing properties of the peptides. Herein "essential" a.a. are defined as those indispensable at said positions for displaying improved LPS-neutralizing properties.

In a preferred embodiment the present invention relates to peptides that bind to and efficaciously neutralize LPS, whose a.a. sequence is derived from the 86-99 a.a. region of the LBP mature protein (SEQ. ID NO.1) but with selected substitutions at particular sites within this domain.

Preferred peptides of the present invention are those with the a.a. sequence X-1-2-3-4-5-6-7-8-9-10-11-12-13-14-Y, wherein:

X is a linear chain from zero to four amino acids.

(1) is one of the a.a. alanine, threonine, glutamine, asparagine or serine, and if and only if at least one of the a.a at positions +5, +9, +10, +11 or +13 has been replaced (from the native sequence) according to what is herein described, then (1) could also be arginine or lysine.

(2) is one of the a.a. alanine, valine, isoleucine, leucine, phenylalanine, methionine, tryptophan or tyrosine.

(3) is one of the a.a. glutamine, asparagine, serine or threonine.

(4) is one of the a.a. glycine, alanine, valine, isoleucine, leucine, phenylalanine, methionine, tryptophan or tyrosine.

(5) is one of the a.a. alanine, threonine, glutamine, asparagine or serine, and if and only if at least one of the a.a. at positions +1, +9, +10, +11 or +13 has been replaced according to what is herein described, then (5) could also be arginine or lysine.

(6) is one of the a.a. tryptophan or phenylalanine.

(7) is one of the a.a. lysine or arginine.

(8) is one of the a.a. alanine, valine, isoleucine, leucine, phenylalanine or tyrosine.

(9) is one of the a.a alanine, threonine, glutamine, asparagine or serine, and if and only if at least one of the a.a. at positions +1, +5, +10, +11 or +13 has been replaced according to what is herein described, then (9) could also be arginine or lysine.

(10) is one of the a.a. alanine, valine, isoleucine, leucine, phenylalanine, methionine, tryptophan or tyrosine, and if and only if at least one of the a.a. at positions +1, +5, +9, +11 6 +13 has been replaced according to what is herein described, then (10) could also be lysine or arginine.

(11) is one of the a.a. alanine or valine; and if and only if at least one of the a.a. at positions +1, +5, +9, +10, 6 +13 has been replaced according to what is herein described, then (11) could also be serine; and if and only if the a.a. at position +10 has been replaced according to what is herein described, then (11) could also be threonine, glutamine, asparagine, lysine or arginine.

(12) is one of the a.a. phenylalanine, tryptophan or tyrosine.

(13) is one of the a.a. alanine, threonine, glutamine, asparagine or serine; and if and only if at least one of the a.a. at positions +1, +5, +9, +10 6 +11 has been replaced according to what is herein described, then (13) could also be phenylalanine, arginine or lysine; and if and only if the a.a at position +14 is lysine or arginine, then (13) could also be glycine.

(14) is one of the a.a. lysine, arginine or alanine, and if and only if the a.a. at position +13 has been replaced according to what is herein described, then (14) could also be valine, isoleucine, leucine, phenylalanine, methionine, tryptophan or tyrosine.

Y is a linear chain from zero to four or amino acids.

The a.a. residues in the previously described preferred peptides could be D- or L-amino acids.

Representative examples of specifically preferred peptides of the present invention include sequences ID No. 2 to 52.

Tests indicate that peptides having the above described sequences show advantageous properties when compared with peptides having other a.a. at the selected sites, or that are substituted at these positions without considering the definitions of the present invention.

Specifically, peptides with the above described sequences have advantageous properties respect to peptides with sequences corresponding to the native LBP protein, or to others including segments of them shorter than 8 a.a.

The functional superiority of the peptides of the present invention respect to previously described peptides[10–14] is based in these single substitutions, and their combinations. These previous reports described peptides derived from LBP with LPS-binding and -neutralizing properties, which could include partially or totally the herein selected sequence, but maintain the LBP native primary sequence or do not involve the essential single or combined substitutions described in the present invention. The neutralizing potency of the peptides described in previous studies, which do not include the essential substitutions as defined in this invention, is various times lower than the potency of the peptides of the present invention, as shown in examples 1 and 3. In addition, peptides that are substituted, in regard to the LBP primary sequence, as defined in SEQ ID No. 53, 54 and 55, or have other a.a different to those defined at the present invention for positions +6, +7 and +12 lack of relevant LPS-neutralizing capacity, as shown in the examples 1 to 3.

Substitutions at the other positions (+1, +5, +9, +10, +11 y+13), as described in the present invention and how illustrate preferred peptides (SEQ ID No. 2 to 52), increased considerably and unexpectedly the peptide ability to block LPS:LBP interaction, and enhanced the inhibitory effect upon LPS-mediated activation of inflammatory cells.

This unexpected quality exhibited by the peptide analogues of the invention differs from the effect of some of those same substitutions within the holoprotein, as described by others[16]. This fact remarks the distinction between the interaction of the peptides of the invention and LPS, and that of LBP, or even its functional N-terminal fragment.

This invention also relates to peptide analogues whit the described sequences which are constrain to adopt a cyclic conformation by means of a disulfide bond formed between two cysteine residues added to their N- and C-terminus respectively, or through an amide bond formed between the side chains of constituting amino acids.

It is further contemplated in this invention that those skill in the art are able to replace particular amino acid residues by non-natural homologous amino acids maintaining the LPS-neutralizing properties of the whole molecule, as well as to change the main chain backbone by backbone-mimetic organic compounds.

In another embodiment this invention relates to larger polypeptides bearing the above described preferred sequences at their N- or C-terminus in such a way that maintains the ability to bind and neutralize LPS and confers this ability to the hybrid polypeptide. A preferred hybrid polypeptide comprises a fusion of any of the preferred peptides and light or heavy chain regions of immunoglobulins (Ig), including the insertion of the peptide sequences of the invention within the framework of the Ig molecule.

This invention also relates to scaffold proteins that appropriately exposed one of the preferred peptide sequences in such a way that maintains or enhances their ability to bind and neutralize LPS and confers this ability to the hybrid polypeptide. The term "scaffold proteins" as herein used refers to hybrid polypeptides that include within their polypeptide chain one or more of the selected sequences in such a way that the inserted segment forms an exposed loop in the structure of the fused protein or polypeptide.

Also this invention relates to two or more repeats of one of the preferred polypeptide sequences in a linear polypeptide chain, or the combination of two or more of them, in such a way that these sequences are connected by linkers, and the novel polypeptide have the ability to bind and efficiently neutralize LPS. Preferred linkers are those having between 12 and 25 amino acid residues and are rich in the glycine, alanine, proline or serine residues. Likewise the present invention applies to arrangements of three or more copies of the preferred peptide sequences linked by their C-terminus to a lysine core, forming structures that have the ability to bind and efficaciously neutralize LPS. Other arrangements of preferred sequences could result from the combination of the aforementioned cyclic peptides.

Synthetic peptides having the described preferred sequences are small molecules with broader utility than larger polypeptides. Particularly, the peptides of the present invention will have some advantages over larger polypeptides concerning immunogenicity and spectrum of LPS-neutralizing activity. In vivo half-life and other pharmacological parameters of the peptides could be improved with hybrid and scaffold polypeptides and proteins bearing the preferred sequences.

All the peptides encompassed by the present invention can be prepared using standard procedures of peptide synthesis, including for example the solid-phase synthetic technique describe by Merrifield[17], as well as other apparent to anyone skilled in the art.

In a further preferred embodiment this invention provides pharmaceutical compositions comprising pharmaceutically appropriated diluents, carriers or adjuvants, and effective quantities of one of more of the peptides, or hybrid or scaffold proteins containing their sequences. The term "effective quantity" as herein used refers to the amount of the peptides, or hybrid or scaffold proteins, that is sufficient to ameliorate symptoms associated with systemic responses to LPS.

The novel pharmaceutical compositions can be useful for methods to treat various disorders associated with the release of LPS, specially the infection with Gram-negative bacteria and its sequelae: endotoxemia and shock, Systemic Inflammatory Response Syndrome (SIRS), Compensatory Anti-inflammatory Response Syndrome (CARS), disseminated intravascular coagulation, Adult Respiratory Distress Syndrome and Multiple Organ Dysfunction Syndrome (MODS). The therapeutic method is provided to ameliorate one or more symptoms of patients suffering or at risk for developing disorders caused by diverse insults such as infection, trauma, burns and pancreatitis. Patients who also may require such a treatment include those afflicted from inflammatory bowel diseases and obstructive jaundice or other disorders where gastrointestinal permeability is impaired and bacterial translocation or endotoxin leakage occur.

EXAMPLES

Example 1

This example describes the capacity of preferred peptides of the invention to block the interaction between LBP and *E. coli* LPS. An ELISA was used to determine the binding of biotinylated-LPS to surface-captured human LBP, in the presence or absence of fixed quantities of the selected peptides. LPS was biotinylated according to standard procedures. Human LBP (hLBP) was captured by using a specific monoclonal antibody, purified by affinity chromatography. Mixtures of LPS and each peptide were incubated during 2 h at room temperature, and then 100 $\mu$L were added to hLBP-containing wells. The binding of biotinylated-LPS to hLBP was detected with horseradish peroxidase-conjugated streptavidin. The assay was developed by adding a chromogenic substrate. FIG. 1 shows the results of this assay when biotinylated-LPS was incubated with peptides $LBP_{86-99}$ (LBP), $LBP_{A86}$ (SEQ ID No.2), $LBP_{A90}$ (SEQ ID No.3) and $LBP_{A94}$ (SEQ ID No.4). FIG. 2 shows results for peptides $LBP_{A95}$ (SEQ ID No.5), $LBP_{A96}$ (SEQ ID No.6) and $LBP_{A98}$ (SEQ ID No.7), and FIG. 3 represents the results for peptides $LBP_{A91}$ (SEQ ID No.55), $LBP_{A92}$ (SEQ ID No.53) and $LBP_{A97}$ (SEQ ID No.54). Each experiment recorded the interaction of hLBP and biotinylated-LPS in absence of peptides, in presence of $LBP_{86-99}$, and in the example presented in FIG. 2 the effect of a non-related cationic peptide (C5,3).

The interaction between hLBP and *E. coli* LPS was notably impaired by peptides of this invention, as represented by $LBP_{A86}$, $LBP_{A90}$, $LBP_{A94}$, $LBP_{A95}$, $LBP_{A96}$ and $LBP_{A98}$, and it was not affected by peptides $LBP_{A91}$, $LBP_{A92}$ and $LBP_{A97}$.

These results demonstrate that peptides with sequences defined as specially preferred in this invention have higher blocking capacity of LBP:LPS interaction than the $LBP_{A86-99}$, that has the native sequence of this region in human LBP. This example confirms that the a.a. substitutions described in the present invention for peptide sequences derived from this particular region of hLBP are essential to obtain peptide analogues that efficaciously block the interaction between hLBP and LPS. Likewise, this example demonstrates that replacements at particular sites of the series, by different a.a. to those described in this invention, reduce or abrogate the LPS-neutralizing activity of peptides derived from the mentioned hLBP region.

Example 2

In order to determine if the peptides of the present invention were able to neutralize LPS-mediated responses, their ability to reduce the release of TNF by LPS-activated human peripheral blood cells was estimated. This assay evaluates the release of TNF by LPS-induced human peripheral blood mononuclear cells (PBMC), using concentrations of LPS commonly found in septic patients. LPS was incubated with fixed concentrations of each peptide during 2 h at 37° C. and the mixtures were then added to PBMC. The culture medium was supplemented with human LBP (200 ng/mL) and plates were incubated at 37° C. in a 5% $CO_2$ atmosphere. TNFα was measured in culture supernatants after 18 h using a human TNF-α specific ELISA. FIG. 4 represents the average results from three different experiments. Reduced levels of cytokine release were observed in cultures containing *E. coli* 0111:B4 LPS and one of the following peptides: $LBP_{86-99}$, $LBP_{A94}$. $LBP_{A95}$ and $LBP_{A96}$. The last three peptides exhibited higher inhibition than $LBP_{86-99}$ (LBP). Similar results were observed when other concentrations of LPS (2 or 10 ng/mL) and hLBP (20 or 100 ng/mL) were used. The non-related, cationic peptide B6,1 did not modify, as expected, the release of TNF in this assay. On the other hand the $LBP_{A91}$ peptide, which has tryptophan residue at position (6) replaced with alanine, did not inhibit LPS-stimulated TNF production.

These results demonstrate that the peptides derived from this region of hLBP should have the specified sequences of this invention for displaying vigorous inhibitory activity upon LPS-mediated activation of human mononuclear cells. Likewise, the results suggest the usefulness of the peptides of the present invention for developing prophylactic and therapeutic methods for sepsis, systemic inflammatory response syndrome and other related disorders. The potency of the preferred peptides of this invention is properly demonstrated in this example, where endotoxin concentrations commonly found in endotoxemic patients were used.

Example 3

This invention provides peptides with advantageous functions over other LBP-derived peptides that have the native sequence or different a.a. replacements to those herein described at positions +1, +5, +6, +7, +9, +10, +11, +12 and +13. Among these others are some peptides previously described by their ability to reduce LPS biological effects[11–14]. In order to demonstrate the advantage of the preferred peptides of this invention over these previously described peptides, their antagonist activity upon LPS-induced responses was compared; the effect of these different peptides on the LPS-induced IL-6 production in cultures of human PBMC is illustrated in FIG. 5. The experimental procedure was similar to that one described in EXAMPLE 2. IL-6 was measured in culture supernatants after 18 h using a human IL-6 specific ELISA. In the represented experiment, the following peptides were evaluated; $LPB_{86-99}$, LBP-H ($LBP_{86-101}$, SEQ ID NO. 56)[13], $LBP_{A94}$, $LBP_{A95}$, and $LBP_{A98}$. IL-6 production was inhibited by more than 35% only by $LBP_{A94}$, $LBP_{A95}$ and $LBP_{A98}$, which have essential a.a. as defined in the present invention at positions +9, +10 and +13 respectively. $LBP_{A95}$ reduced the LPS-triggered response more than 70%, at every hLBP concentrations tested. This example remarks the capacity of the peptides or this invention to reduce the production of pro-inflammatory cytokines by LPS-stimulated cells.

Example 4

An endotoxin shock animal model was used to determine if the peptides of this invention were able to block complex physiological responses triggered by LPS. In this model mice were sensitized with Actinomycin D to increase LPS-mediated toxic responses. With this purpose, Actinomycin D (7.5 μg) was administered i.p. to 6 to 8 weeks-old female mice. Simultaneously each mice received LPS, and survival was evaluated every 24 h during 120 h.

The effect of peptides of the present invention on mice survival was assessed by administering *E. coli* LPS (1 μg/mouse in saline vehicle) or LPS:peptide mixtures mixtures (previously incubated during 1 h at 37° C.) to BALB/c sensitized mice. FIG. 6 represents the results of a representative experiment where the following peptides were each administered at equimolar doses to groups of 20 mice: $LBP_{86-99}$, $LBP_{A94}$, $LBP_{As95}$, $LBP_{A98}$ or B6, 1 (cationic, non-related peptide). Mice survival was only significantly increased by $LBP_{A94}$, $LBP_{A95}$ or $LBP_{A98}$ (*$p<0.05$ vs. vehicle or B6,1). The peptide $LBP_{86-99}$ increase survival only marginally. This example demonstrates the higher efficacy of preferred peptides of this invention in protecting mice from LPS lethal inocula. The aforementioned in vivo neutralizing property of the peptides of the invention is relevant for their application in prophylactic or therapeutic methods for sepsis and other associated disorders.

Thus the above-mentioned results indicate that peptides of this invention retain their LPS-blocking properties when tested under patho-physiological conditions, demonstrating their pharmacological potency.

BRIEF DESCRIPTION OF THE DRAWINGS

Analogues of Lipopolysaccharide-Binding Protein (LBP)-Derived Peptides that Efficiently Neutralize Lipopolysaccharides (LPS).

REFERENCES

Figure 1:
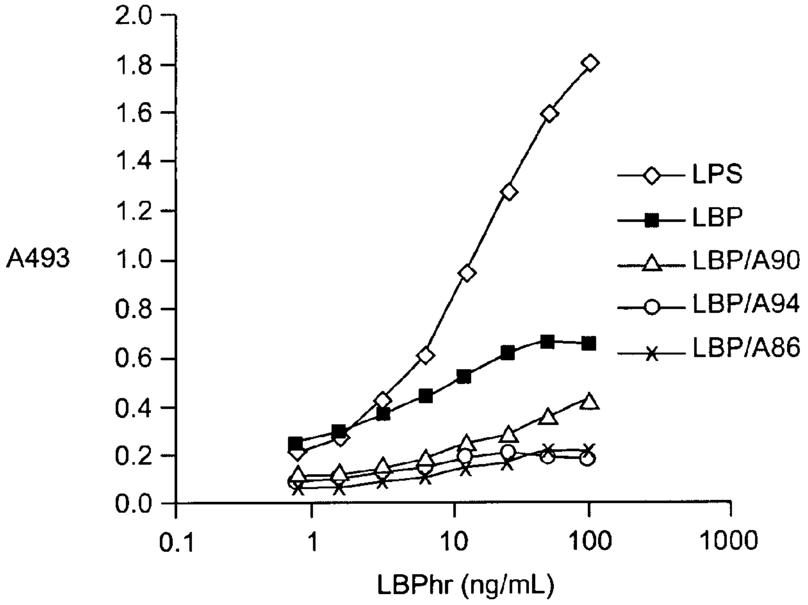
FIG. 1 shows the inhibition of the interaction between *E. coli* LPS and hLBP by preferred peptides of the present invention ($LBP_{A86}$, $LBP_{A90}$ and $LBP_{A94}$). Human LBP was captured to the plates using a specific monoclonal antibody. Binding of biotinylated-LPS was detected with an streptavidin-horseradish peroxidase conjugate. The extent to which the peptide $LBP_{86-99}$ (LBP) inhibits this interaction is also shown.
Figure 2:
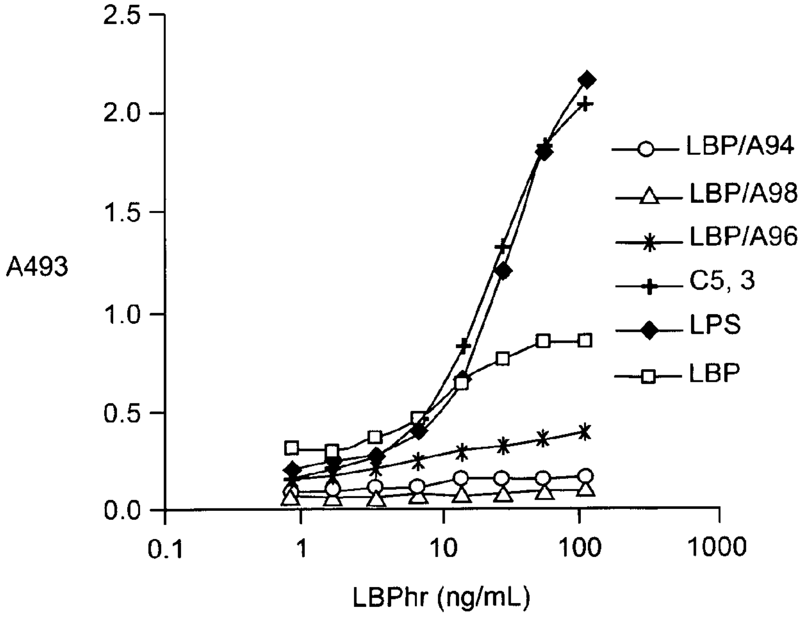
FIG. 2 shows the inhibition of the interaction between *E. coli* LPS and hLBP by preferred peptides of the present invention ($LBP_{A95}$, $LBP_{A96}$ and $LBP_{A98}$). The experimental conditions were similar to those described in FIG. 1. The effect of a non-related cationic peptide, C5,3 is also included.
Figure 3:
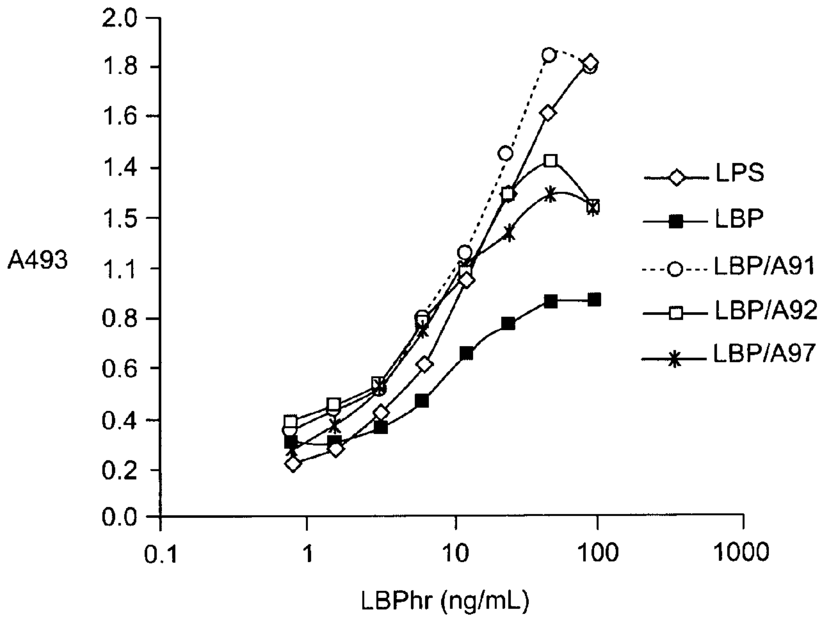
FIG. 3 shows the effect on the interaction of hLBP and *E. coli* LPS of peptides that have distinct residues at positions +6, +7 or +12 to those described in this invention ($LBP_{A91}$, $LBP_{A92}$ and $LBP_{A97}$) The experimental conditions were similar to those described in FIG. 1.
Figure 4:
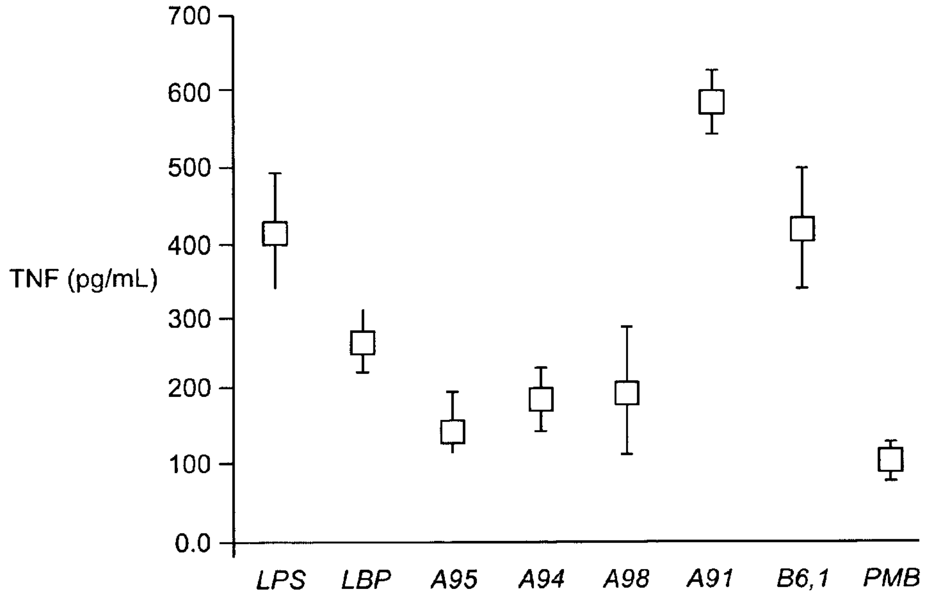
FIG. 4 shows the inhibition by peptides of the present invention ($LBP_{A94}$, $LBP_{A95}$ and $LBP_{A98}$) of the LPS-mediated release of TNF by human PBMC. The effects on this assay of $LBP_{86-99}$ (LBP), $LBP_{A91}$, B6,1 and polymyxin B (PMB) are also shown.
Figure 5:
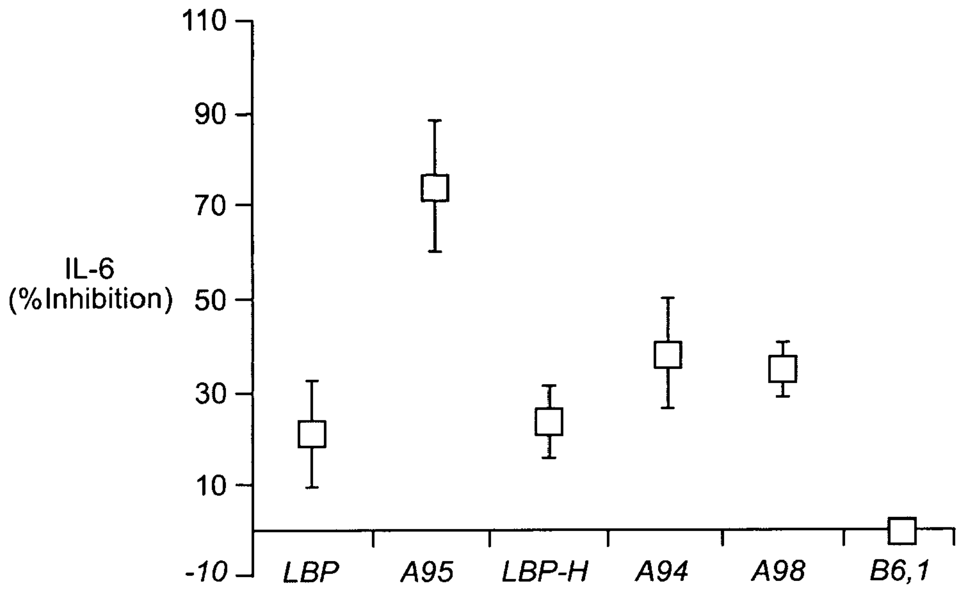
FIG. 5 shows the inhibition by peptides of the present invention ($LBP_{A94}$, $LBP_{A95}$ and $LBP_{A98}$) of the LPS-mediated release of IL-6 by human PBMC. Results are expressed as % inhibition of IL-6 release compared with the cytokine production in the absence of peptides The effects on this assay of $LBP_{86-99}$, (LBP), LBP-H and B6,1 are also shown.
Figure 6:
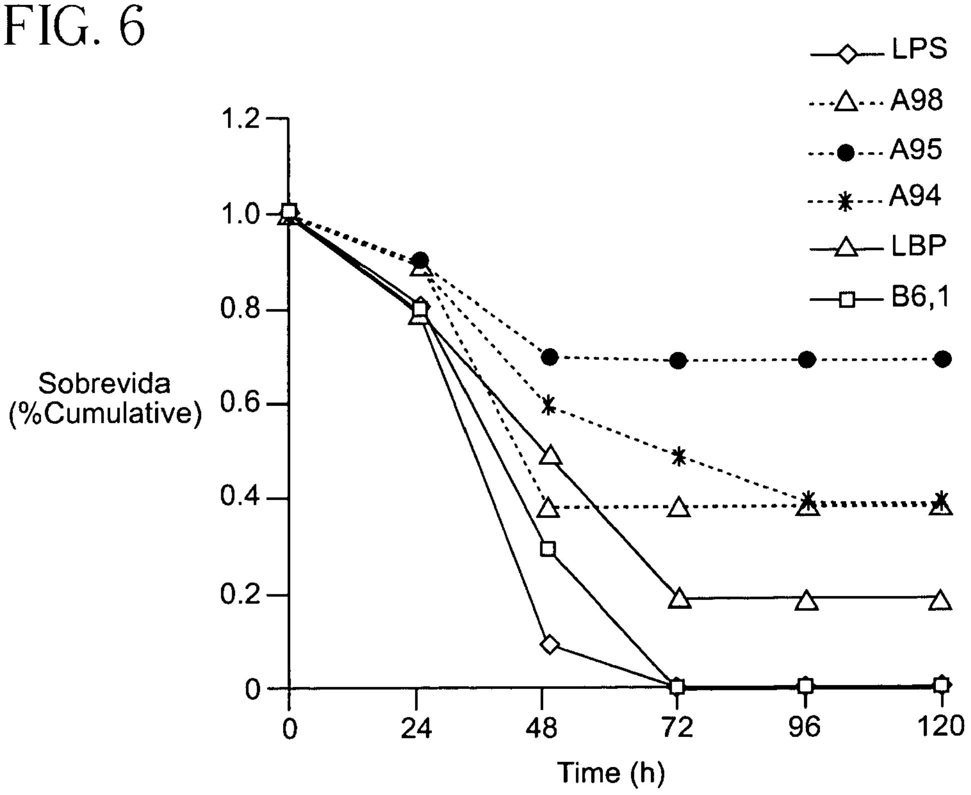
FIG. 6 shows survival data of groups of 20 mice each challenged with *E. coli* LPS i.p. and simultaneously treated with equimolar amounts of different peptides of the present invention. Survival in groups of BALB/c mice treated with $LBP_{86-99}$ (LBP) and B6,1 is also shown. Mice survival was recorded each 24 h during 120 h.

1. Wright, S D, Ramos, R A, Tobias, P S, Ulevitch, R J, Mathison, J C (1990). CD14 serves as the cellular receptor for complexes of lipopolysaccharide with lipopolysaccharide binding protein. *Science* 249:1431–33.
2. Pugin, J. Schurer-Maly, C C, Leturcq, D, Moriarty, A, Ulevitch, R J, Tobias, P S (1993). LPS activation of human endothelial and epithelial cells is mediated by LPS binding protein and soluble CD14. *Proc. Natl. Acad. Sci USA* 90:2744–48.
3. Mathinson, J. C., Wolfson, E. y Ulevitch, R. J. (1988). Participation of tumor necrosis in the mediation of Gram-negative bacteria lipopolysaccharide-induced injury in rabbits. *J. Clin. Invest.* 81:1925–37
4. Weiss, J., Elsbach, P., Shu, C., Castillo, J., Grinna, L., Horwitz, A., Theofan, G. (1992). Human bactericidal/permeability increasing protein and a recombinant NH2-terminal fragment cause killing of serum-resistant gram-negative bacteria in whole blood and inhibit tumor necrosis factor release induced by bacteria. *J. Clin. Invest.* 90:1122–30
5. Little, R. G., Kelner, D. N., Lim, E., Burke, D. J., Conlon, P. J. (1994). Functional domains of recombinant bactericidal/permeability increasing protein. *J. Biolog. Chem.* 269(3):1865–72
6. Battafarano, R. J., Dahlberg, P. S., Ratz, C. A., Johnston, J. W., Gray, B. H., Haseman, J. R., Mayo, K. H., Dunn, D. L. (1995). Peptide derivatives of three distinct lipopolysaccharide binding proteins inhibit LPS-induced tumor necrosis factor-alpha secretion in vitro. *Surgery* 118:318–24.
7. Dahlberg, P. S., Acton, R. D., Battafarano, R. J., Uknis, M. E., Ratz, C. A. Johnston, J. W., Haseman, J. R., Gray, B. H., Dunn, D. L. (1996). A novel endotoxin antagonist attenuates tumor necrosis factor-alpha secretion. *J. Surg. Res.* 63.44–48
8. Uknis, M. E., Wasiluk, K. R., Acton, R. D., Klaerner, H. G., Dahlberg, P. S., Ilyina, E. E., Haseman, J. R., Gray, B. H., Mayo, K. H., Dunn, D. L. (1997). Design of a potent novel endotoxin antagonist. *Surgery* 122:380–5
9. Ried, C., Wahl, C., Miethke, T., W Ilnhofer, G., Landgraf, C., Scheneider-Mergener, J., Hoess, A. (1996). High affinity endotoxin-binding and neutralizing peptides based on the crystal structure of recombinant *Limulus* anti-LPS factor. *J. Biol. Chem.* 271(45):28120–127.
10. Han, J., Ulevitch, R., Tobias, P. (1995). Polypeptides of lipopolysac-charide binding protein. WO 95/25117.
11. Heavner, G. A., Taylor, A., Sgerris, D. (1994). Novel peptides useful for inhibiting binding of LPS by LPS-binding protein. WO 95/06560.
12. Gazzano-Santoro, H., Theofan, G., Trown, P. W. (1995). Lipopolysaccharide binding protein derivatives. WO 95/00641
13. Hoess, A., Liddington, R. C. (1995). Lipopolysaccharide-binding and neutralizing peptides. WO 95/05393.
14. Araña, M. J., Chinea, G., Guerra, M. y Rodríguez, A. Péptidos derivados de la proteína que enlaza LPS, que neutralizan la activación celular mediada por LPS y mejoran las afecciones relacionadas con la endotoxina (1997). OCPI 128/97
15. Hoess, A., Watson, S., Siber, G. R., Liddington, R. (1993). Crystal structure of an endotoxin-neutralizing protein from horseshoe crab, *Limulus* anti-LPS factor, at 1.5 Å resolution. *EMBO J.* 12(9):3351–56.
16. Lamping, N., Hoess, A., Yu, B., Park, T. C., Kirschning, C. J., Pfeil, D., Reuter, D., Wright, S. D., Herrmann, F., Schumann, R. R. (1996). Effects of site-directed mutagenesis of basic residues (Arg94, Lys95, Lys99) of LPS-binding protein on binding and transfer of LPS and subsequent immune cell activation. *J. Immunol.* 157:4648–56
17. Merrifield, R. B. (1963) *J. Amer. Chem. Soc.* 1963, 85:2149–2154

---

The invention claimed is:

1. A purified peptide having LPS-binding and -neutralizing activity wherein the peptide is derived from SEQ ID NO: 1 by modification of one amino acid residue in SEQ ID NO:1 to obtain a modified peptide, and optionally, by extension of up to four residues at each side of the modified peptide; and wherein said modification is an amino acid substitution selected from the group consisting of:

(i) replacement of Arg at position 1 by one of the D- or L-amino acid residues Ala, Thr, Gln, Asn or Ser;

(ii) replacement of Arg at position 5 by one of the D- or L-amino acid residues Ala, Thr, Gln, Asn or Ser;

(iii) replacement of Arg at position 9 by one of the D- or L-amino acid residues Ala, Thr, Gln, Asn or Ser;

(iv) replacement of Lys at position 10 by one of the D- or L-amino acid residues Ala, Val, Ile, Leu, Phe, Met, Trp or Tyr;

(v) replacement of Ser at position 11 by one of the D- or L-amino acid residues Ala or Val; and (vi) replacement of Phe at position 12 by one of the D- or L-amino acid residues Ala, Thr, Gln, Asn or Ser.

2. A purified peptide according to claim 1, wherein said peptide constitutes the N-terminal region of a larger polypeptide.

3. A purified peptide according to claim 1, wherein said peptide constitutes the C-terminal region of a larger polypeptide.

4. A purified peptide according to claim 1, wherein said peptide is inserted into a larger polypeptide.

5. A purified peptide according to claim 1, wherein at least one amino acid of said peptide is substituted by a non-natural homologous amino acid.

6. A purified peptide according to claim 2, wherein the N-terminus is modified by acetylation or succinylation.

7. A purified peptide according to claim 3, wherein the C-terminus is a —OH, —COOH or —$CONH_2$ group.

8. A purified peptide according to claim 1, wherein said peptide is constrained to adopt a cyclic conformation by an intramolecular disulfide or amide bond.

9. A purified peptide according to claim 1, wherein the backbone of said peptide is substituted by backbone-mimetic organic entities.

10. A purified peptide according to claim 1, wherein at least one amino acid of said peptide is substituted by alkylation using chemical or enzymatic methods.

11. A purified peptide according to claim 1, wherein at least one amino acid of said peptide is glycosylated using chemical or enzymatic methods.

12. A purified peptide according to claim 1, wherein said peptide further comprises a label selected from the group consisting of biotin, radioisotopes, enzymes, colloidal metals or fluorescent, chemiluminescent, or phosphorescent compounds.

13. A linear polypeptide chain containing two or more repeats of a purified peptide according to claim 1, wherein said repeats of the peptide are connected by 12–25 amino acid linkers, rich in glycine, alanine, proline or serine residues.

14. A linear polypeptide chain containing a combination of two or more purified peptides according to claim 1, wherein said combination of the peptides is connected by 12–25 amino acid linkers, rich in glycine, alanine, proline or serine residues.

15. An arrangement of three or more purified peptides according to claim 1, wherein said peptides are linked by their C-terminus to a lysine core structure.

* * * * *

UNITED STATES PATENT AND TRADEMARK OFFICE

CERTIFICATE OF CORRECTION

PATENT NO. : 7,012,127 B1
APPLICATION NO. : 09/588525
DATED : March 14, 2006
INVENTOR(S) : Arana Rosainz et al.

It is certified that error appears in the above-identified patent and that said Letters Patent is hereby corrected as shown below:

<u>IN THE PATENT:</u>

In Column 7, line 36: now reads "and $LBP_{A96}$"
should read --and $LBP_{A98}$--

In Column 8, line 36: now reads "$LBP_{AS95}$"
should read --$LBP_{A95}$--

Signed and Sealed this

Twenty-second Day of August, 2006

JON W. DUDAS
*Director of the United States Patent and Trademark Office*